(12) United States Patent
    Gao

(10) Patent No.: US 12,605,726 B2
(45) Date of Patent: Apr. 21, 2026

(54) ATOMIZING HEAD BAFFLE AND FRAGRANCE DIFFUSER

(71) Applicant: Guangdong Chiyang Scent Technology Co., LTD., Foshan (CN)

(72) Inventor: Xiaoyang Gao, Foshan (CN)

(73) Assignee: Guangdong Chiyang Scent Technology Co., LTD., Foshan (CN)

( * ) Notice: Subject to any disclaimer, the term of this patent is extended or adjusted under 35 U.S.C. 154(b) by 7 days.

(21) Appl. No.: 19/083,635

(22) Filed: Mar. 19, 2025

(65) Prior Publication Data

US 2026/0008067 A1     Jan. 8, 2026

(30) Foreign Application Priority Data

Jul. 4, 2024   (CN) .......................... 202421571909.8

(51) Int. Cl.
    *A61L 9/14*        (2006.01)
    *B05B 1/28*        (2006.01)

(52) U.S. Cl.
    CPC ...... *B05B 1/28* (2013.01); *A61L 9/14* (2013.01); *A61L 2209/134* (2013.01)

(58) Field of Classification Search
    CPC .............................. A61L 9/14; A61L 2209/134
    USPC ........ 239/340, 343, 346, 499, 500, 504, 518
    See application file for complete search history.

(56) References Cited

U.S. PATENT DOCUMENTS

| | | | | | |
|---|---|---|---|---|---|
| 4,759,501 | A | * | 7/1988 | Silvenis ..................... | A61L 9/14 239/289 |
| 6,776,968 | B2 | * | 8/2004 | Edwards ................... | A61L 9/03 422/126 |
| 2019/0217026 | A1 | * | 7/2019 | Ye ............................. | A61L 9/14 |
| 2024/0207479 | A1 | * | 6/2024 | Long ......................... | A61L 9/14 |

* cited by examiner

*Primary Examiner* — Devon C Kramer
*Assistant Examiner* — Sean V Meiller
(74) *Attorney, Agent, or Firm* — Hemisphere Law, PLLC

(57)                ABSTRACT

An atomizing head baffle includes a first baffle plate and a second baffle plate. A cover plate is disposed on a top of the first baffle plate. The first baffle plate defines first through-holes spaced along a circumferential direction of the first baffle plate. The second baffle plate defines second through-holes spaced along a circumferential direction of the second baffle plate. The second baffle plate is sleeved around an outer periphery of the first baffle plate, thereby reducing areas of the second through-holes to form air holes, and the air holes and the first through-holes are configured to pass through atomized particles. By changing numbers and/or sizes of the first through-holes and the air holes, an atomization amount and an atomization particle size can be changed to meet needs of users without changing other structural parameters or affecting other internal components. This is relatively simple and low cost.

13 Claims, 3 Drawing Sheets

ATOMIZING HEAD BAFFLE AND FRAGRANCE DIFFUSER

CROSS-REFERENCE TO RELATED APPLICATION

This application claims priority to Chinese Patent Application No. 202421571909.8, filed Jul. 4, 2024, which is herein incorporated by reference in its entirety.

TECHNICAL FIELD

The disclosure relates to the technical field of fragrance devices, and more particularly to an atomizing head baffle and a fragrance diffuser.

BACKGROUND

At present, a fragrance device on the market usually atomizes perfume or essential oil and other fresheners at an atomizer through a principle of negative pressure, and then diffuses fragrance into air through an atomizer outlet, thereby improving air quality.

Atomization amount and atomization particle size are two important product indicators for the fragrance device. The smaller the atomization particle size, the larger a diffusion range, and then the larger an air improvement range of the fragrance device. On the contrary, if the atomization particle size is larger, not only is the air improvement effect limited, but a surface of the fragrance device is also prone to essential oil deposition, causing inconvenience in use. The atomization amount is a fundamental and decisive indicator for air improvement. Different users of a same product may have different needs for the atomization amount and the atomization particle size. How to meet the different needs of the users at a lower cost has become an urgent problem to be solved.

SUMMARY

In view of this, a purpose of the disclosure is to provide an atomizing head baffle (also referred to as atomizer head baffle) and a fragrance diffuser to solve a problem of how to meet different needs of users for atomization amount and atomization particle size at a lower cost.

In order to solve the above technical problems, the technical solutions adopted by the disclosure are as follows.

An atomizing head baffle provided by the disclosure is configured to be used in a fragrance device and is disposed between an atomizing core and a mist outlet of the fragrance device; the atomizing head baffle includes a first baffle plate and a second baffle plate, the first baffle plate and the second baffle plate are ring-shaped, and a cover plate is disposed on a top of the first baffle plate and is protruding; the first baffle plate defines first through-holes extending from a lower edge to an upper edge and spaced along a circumferential direction of the first baffle plate, and a number of the first through-holes is at least two; and the second baffle plate defines second through-holes extending from a lower edge to an upper edge and spaced along a circumferential direction of the second baffle plate, and a number of the second through-holes is at least two; and the second baffle plate is sleeved around an outer periphery of the first baffle plate with a preset overlapping distance, thereby reducing areas of the second through-holes to form air holes, and the air holes and the first through-holes are configured to pass through atomized particles.

In an embodiment, widths of the first through-holes and the second through-holes are equal.

In an embodiment, the first through-holes are disposed uniformly along the circumferential direction of the first baffle plate, the second through-holes are disposed uniformly along the circumferential direction of the second baffle plate, the number of the first through-holes is six, and the number of the second through-holes is three.

In an embodiment, widths of the air holes and the first through-holes are in a range of 6 millimeters (mm) to 12 mm, and heights of the air holes and the first through-holes are in a range of 2 mm to 6 mm.

In an embodiment, widths of the air holes are in a range of 5.5 mm to 6.5 mm, and heights of the air holes are in a range of 1.5 mm to 2.5 mm; and widths of the first through-holes are in a range of 5.5 mm to 6.5 mm, and heights of the first through-holes are in a range of 4.5 mm to 5.5 mm; or the widths of the air holes are in a range of 7.5 mm to 8.5 mm, and the heights of the air holes are in a range of 2.5 mm to 3.5 mm; and the widths of the first through-holes are in a range of 7.5 mm to 8.5 mm, and the heights of the first through-holes are in a range of 5.5 mm to 6.5 mm; or the widths of the air holes are in a range of 8.5 mm to 9.5 mm, and the heights of the air holes are in a range of 2.5 mm to 3.5 mm; and the widths of the first through-holes are in a range of 8.5 mm to 9.5 mm, and the heights of the first through-holes are in a range of 5.5 mm to 6.5 mm; or the widths of the air holes are in a range of 9.5 mm to 10.5 mm, and the heights of the air holes are in a range of 2.5 mm to 3.5 mm; and the widths of the first through-holes are in a range of 9.5 mm to 10.5 mm, and the heights of the first through-holes are in a range of 5.5 mm to 6.5 mm; or the widths of the air holes are in a range of 11.5 mm to 12.5 mm, and the heights of the air holes are in a range of 2.5 mm to 3.5 mm; and the widths of the first through-holes are in a range of 11.5 mm to 12.5 mm, and the heights of the first through-holes are in a range of 5.5 mm to 6.5 mm.

A fragrance diffuser further provided by the disclosure includes an atomizing head assembly, and the atomizing head assembly includes the atomizing head baffle described above.

In an embodiment, the atomizing head assembly further includes a main body, an essential oil bottle and a cover, the main body is provided with an atomizing core, a cavity and an air passage, the air passage and the cavity are connected to the atomizing core separately, an atomizing head liner located above the atomizing core is disposed in the cavity, the atomizing head baffle is located in the cavity, and the atomizing head baffle is disposed above the atomizing head liner and is in contact with the atomizing head liner; and a lower end of the main body is connected to the essential oil bottle, and an upper end of the main body is connected to the cover; and the cover is configured to fix the atomizing head baffle and the atomizing head liner in the cavity, and the cover is defined with a mist outlet connected to the cavity.

In an embodiment, the fragrance diffuser further includes a locking member and an outer shell, and an inner shell is disposed in the outer shell; an engagement groove is defined on an outer side of the inner shell and is protruding outward, an end of the locking member is rotatably penetrated a side wall of the inner shell, and the end of the locking member is provided with a locking hook; and the atomizing head assembly is inserted into the inner shell, and the atomizing head assembly remains stable relative to the inner shell when the locking hook is engaged with the engagement groove.

In an embodiment, the fragrance diffuser further includes an air pump assembly, a base is disposed on a bottom of the outer shell, and the air pump assembly is disposed in the outer shell and is connected to the base.

In an embodiment, an antiskid pad is disposed on a bottom of the base.

Compared to the related art, the main beneficial effects of the atomizing head baffle provided by the disclosure are as follows.

The atomizing head baffle provided by the disclosure is provided with at least two first through-holes on the first baffle plate and at least two second through-holes on the second baffle plate. The second baffle plate is sleeved around the outer periphery of the first baffle plate with the preset overlapping distance to form the air holes. By changing numbers and/or sizes of the first through-holes and the air holes, an atomization amount and an atomization particle size can be changed, thereby meeting different needs of users for the atomization amount and the atomization particle size. There is no need to adjust other structural parameters, nor will it affect a structure of other components inside the fragrance diffuser. Compared to a method of modifying an internal structure of the fragrance diffuser to change the atomization amount and the atomization particle size, this method is relatively simple and low cost.

Compared to the related art, the main beneficial effects of the fragrance diffuser provided by the disclosure are as follows.

The fragrance diffuser of the disclosure adopts the atomizing head baffle described above, thus having the beneficial effects of the atomizing head baffle, which will not be further described.

BRIEF DESCRIPTION OF DRAWINGS

Through the specific embodiments of the disclosure shown in the accompanying drawings, the above and other purposes, features, and advantages of the disclosure will become clearer. In all the accompanying drawings, the same reference numerals indicate the same parts. The accompanying drawings are not drawn to scale, with emphasis on illustrating the principles of the disclosure.

Figure 1:
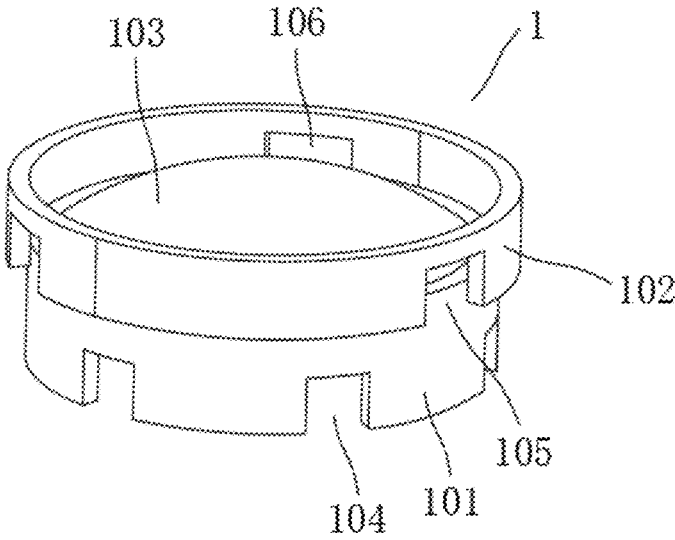
FIG. 1 illustrates a perspective view of an atomizing head baffle provided by an embodiment of the disclosure.
Figure 2:
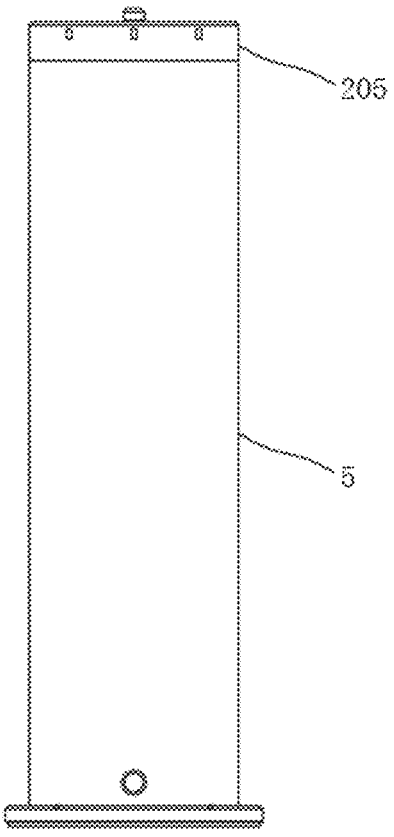
FIG. 2 illustrates a perspective view of a fragrance diffuser provided by the embodiment of the disclosure.

Descriptions of numeral signs: 1, atomizing head baffle; 101, first baffle plate; 102, second baffle plate; 103, cover plate; 104, first through-hole; 105, second through-hole; 106, air hole; 2, atomizing head assembly; 201, atomizing core; 202, mist outlet; 203, main body; 204, essential oil bottle; 205, cover; 206, cavity; 207, air passage; 208, atomizing head liner; 3, locking member; 4, locking hook; 5, outer shell; 6, inner shell; 7, engagement groove; 8, air pump assembly; 9, base; and 10, antiskid pad.

DETAILED DESCRIPTION OF EMBODIMENTS

The following provides a further detailed description of the technical solution of the disclosure in conjunction with the accompanying drawings and specific embodiments, in order to enable those skilled in the art to better understand and implement the disclosure. However, the embodiments provided are not intended to limit the disclosure. In the embodiment, it should be understood that the terms "longitudinal", "transverse", "up", "down", "front", "back", "left", "right", "vertical", "horizontal", "top", "bottom", "inside", "outside", etc., which indicate orientations or positional relationships, are based on the orientations or positional relationships shown in the drawings. These terms are used only for the convenience of describing the disclosure and are not intended to indicate or imply that the device or components must have a specific orientation, be constructed and operated in a specific orientation, and therefore should not be construed as a limitation of the disclosure.

It should be noted that when an element is considered to be "connected" to another element, it can be directly connected to and integrated with the another element, or there may be intermediate elements present. The terms "mounted", "one end", "another end", and similar expressions used in the disclosure are for illustrative purposes only.

In an embodiment, an atomizing head baffle is provided. As shown in FIG. 1, the atomizing head baffle 1 is used in a fragrance device and is disposed between an atomizing core 201 and a mist outlet 202 of the fragrance device. The atomizing head baffle 1 includes a first baffle plate 101 and a second baffle plate 102 which are ring-shaped. A cover plate 103 is disposed on a top of the first baffle plate 101 and is protruding. The first baffle plate 101 defines at least two first through-holes 104 extending from a lower edge to an upper edge and spaced along a circumferential direction of the first baffle plate 101. The second baffle plate 102 defines at least two second through-holes 105 extending from a lower edge to an upper edge and spaced along a circumferential direction of the second baffle plate 102.

The second baffle plate 102 is sleeved around an outer periphery of the first baffle plate 101 with a present overlapping distance, thereby reducing areas of the second through-holes 105 to form air holes 106. The air holes 106 and the first through-holes 104 are configured to pass through atomized particles.

The atomizing head baffle provided by the disclosure is provided with the at least two first through-holes 104 on the first baffle plate 101 and the at least two second through-holes 105 on the second baffle plate 102. The second baffle plate 102 is sleeved around the outer periphery of the first baffle plate 101 with the preset overlapping distance to form the air holes 106. By changing numbers and/or sizes of the first through-holes 104 and the air holes 106, an atomization amount and an atomization particle size can be changed, thereby meeting different needs of users for the atomization amount and the atomization particle size. There is no need to adjust other structural parameters, nor will it affect a structure of other components inside the fragrance diffuser. Compared to a method of modifying an internal structure of the fragrance diffuser to change the atomization amount and the atomization particle size, this method is relatively simple and low cost.

In addition, the cover plate 103 protruding on the top of the first baffle plate 101 can promote the atomized particles to pass through the first through-holes 104 and the air holes 106, serving a function of screening the atomized particles. Moreover, it also has a certain noise-reducing effect and can quickly collect the atomized particles that fall on an upper surface of the cover plate 103 downwards for recycling and reuse.

In a specific embodiment, widths of the first through-holes 104 and the second through-holes 105 are equal. By setting widths of holes (i.e., the first through-holes 104 and the second through-holes 105) as a constant value and adjusting heights of the holes, different atomization amounts and atomization particle sizes are obtained. Since sizes of the holes is usually measured in millimeters, it can reduce processing difficulty and simplify a testing process by reducing variables.

In another specific embodiment, widths of the air holes 106 and the first through-holes 104 are in a range of 6 mm to 12 mm, and heights of the air holes 106 and the first through-holes 104 are in a range of 2 mm to 6 mm. This design can achieve a larger atomization amount and ensure a smaller atomization particle size, thus solving a problem of not being able to have both the large atomization amount and the small atomization particle size.

In an illustrative embodiment, the number of the first through-holes 104 is six, and the number of the second through-holes 105 is three. Furthermore, widths of the air holes 106 are in a range of 5.5 mm to 6.5 mm, and heights of the air holes 106 are in a range of 1.5 mm to 2.5 mm; and widths of the first through-holes 104 are in a range of 5.5 mm to 6.5 mm, and heights of the first through-holes 105 are in a range of 4.5 mm to 5.5 mm.

Alternatively, the widths of the air holes 106 are in a range of 7.5 mm to 8.5 mm, and the heights of the air holes 106 are in a range of 2.5 mm to 3.5 mm; and the widths of the first through-holes 104 are in a range of 7.5 mm to 8.5 mm, and heights of the first through-holes 105 are in a range of 5.5 mm to 6.5 mm.

Alternatively, the widths of the air holes 106 are in a range of 8.5 mm to 9.5 mm, and the heights of the air holes 106 are in a range of 2.5 mm to 3.5 mm; and the widths of the first through-holes 104 are in a range of 8.5 mm to 9.5 mm, and the heights of the first through-holes 105 are 5.5 mm to 6.5 mm.

Alternatively, the widths of the air holes 106 are in a range of 9.5 mm to 10.5 mm, and the heights of the air holes 106 are in a range of 2.5 mm to 3.5 mm; and the widths of the first through-holes 104 are in a range of 9.5 mm to 10.5 mm, and the heights of the first through-holes 105 are in a range of 5.5 mm to 6.5 mm.

Alternatively, the widths of the air holes 106 are in a range of 11.5 mm to 12.5 mm, and the heights of the air holes 106 are in a range of 2.5 mm to 3.5 mm; and the widths of the first through-holes 104 are in a range of 11.5 mm to 12.5 mm, and the heights of the first through-holes 105 are in a range of 5.5 mm to 6.5 mm.

The above combinations of the air holes 106 and the first through-holes 104 can all achieve an average atomization amount of more than 3 liters (L), and meet a need of an average atomization particle size of X4:3 of less than 3 micrometers (μm).

In a specific embodiment, the first through-holes 105 are disposed uniformly along the circumferential direction of the first baffle plate 101, and the second through-holes 105 are disposed uniformly along the circumferential direction of the second baffle plate 102, ensuring that the atomized particles can float out evenly.

Based on the aforementioned atomizing head baffle, an embodiment of a fragrance diffuser is provided. As shown in FIGS. 2-6, the fragrance diffuser includes an atomizing head assembly 2, and the atomizing head assembly 2 includes the atomizing head baffle 1 described above. In the embodiment of the fragrance diffuser, the atomization amount and the atomization particle size can be changed by changing the numbers and the sizes of the first through-holes 104 and the air holes 106 of the atomizing head baffle 1. Specifically, after testing, it is indicated that the atomization amount and the atomization particle size increase with an enlargement of diameters of the holes.

Figure 3:
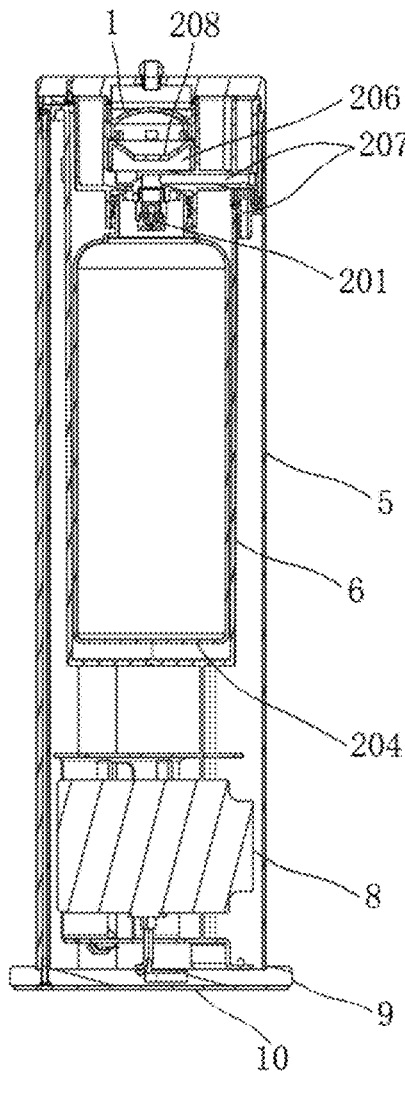
FIG. 3 illustrates a cross-sectional view of the fragrance diffuser provided by the embodiment of the disclosure.

In a specific embodiment, the atomizing head assembly 2 further includes a main body 203, an essential oil bottle 204 and a cover 205. The main body 203 is provided with an atomizing core 201, a cavity 206 and an air passage 207. The air passage 207 and the cavity 206 are connected to the atomizing core 201 separately. An atomizing head liner 208 located above the atomizing core 201 is disposed in the cavity 206. The atomizing head baffle 1 is located in the cavity 206, and the atomizing head baffle 1 is disposed above the atomizing head liner 208 and is in contact with the atomizing head liner 208. A lower end of the main body 203 is connected to the essential oil bottle 204, and an upper end of the main body 203 is connected to the cover 205. The cover 205 is configured to fix the atomizing head baffle 1 and the atomizing head liner 208 in the cavity 206. The cover 205 is defined with a mist outlet 202 connected to the cavity 206. Specifically, as shown in FIG. 3, the atomizing head liner 208 is funnel-shaped with an opening in a middle. On one hand, it serves to reduce noise, and on the other hand, it facilitates a timely recovery of larger atomized particles that settle and fall into the essential oil bottle 204.

In an embodiment, essential oils and other fresheners are atomized at the atomizing core 201 through a principle of negative pressure. The atomized particles will float out of the essential oil bottle 204 and enter the cavity 206, passing through an opening of the atomized head liner 208 and the first through-holes 104 and the air holes 106 of the atomizing head baffle 1 sequentially, and finally float out from the mist outlet 202. It should be noted that, after testing, the number of the air holes 106 in the embodiment of the fragrance diffuser is three and the number of first through-holes 104 is six.

When the widths of the air holes 106 are 6±0.5 mm, the heights of the air holes are 2±0.5 mm, the widths of the first through-holes 104 are 6±0.5 mm, the heights of the first through-holes 104 are 5±0.5 mm, the average atomization amount can reach 3.25 L, an average atomization particle size of Xv50 can reach 2.17 micrometers (μm), and the average atomization particle size of the X4:3 can reach 2.68 μm.

When the widths of the air holes 106 are 8±0.5 mm, the heights of the air holes are 3±0.5 mm, the widths of the first through-holes 104 are 8±0.5 mm, the heights of the first through-holes 104 are 6±0.5 mm, the average atomization amount can reach 3.63 L, the average atomization particle size of the Xv50 can reach 2.16 μm, and the average atomization particle size of the X4:3 can reach 2.88 μm.

When the widths of the air holes 106 are 9±0.5 mm, the heights of the air holes are 3±0.5 mm, the widths of the first through-holes 104 are 9±0.5 mm, the heights of the first through-holes 104 are 6±0.5 mm, the average atomization amount can reach 4.08 L, the average atomization particle size of the Xv50 can reach 2.19 µm, and the average atomization particle size of the X4:3 can reach 2.70 µm.

When the widths of the air holes 106 are 10±0.5 mm, the heights of the air holes are 3±0.5 mm, the widths of the first through-holes 104 are 10±0.5 mm, the heights of the first through-holes 104 are 6±0.5 mm, the average atomization amount can reach 4.2 L, the average atomization particle size of the Xv50 can reach 2.03 µm, and the average atomization particle size of the X4:3 can reach 2.45 µm.

When the widths of the air holes 106 are 12±0.5 mm, the heights of the air holes are 3±0.5 mm, the widths of the first through-holes 104 are 12±0.5 mm, the heights of the first through-holes 104 are 6±0.5 mm, the average atomization amount can reach 4.57 L, the average atomization particle size of the Xv50 can reach 2.30 µm, and the average atomization particle size of the X4:3 can reach 2.95 µm.

It should be noted that the Xv50 represents an average size value of 50% of the atomized particles, X4:3 represents an average size value of all atomized particles. Conventional testing instruments are used for testing, a testing temperature is 25±5° C., and a testing humidity is 40% to 70%.

Figure 4:
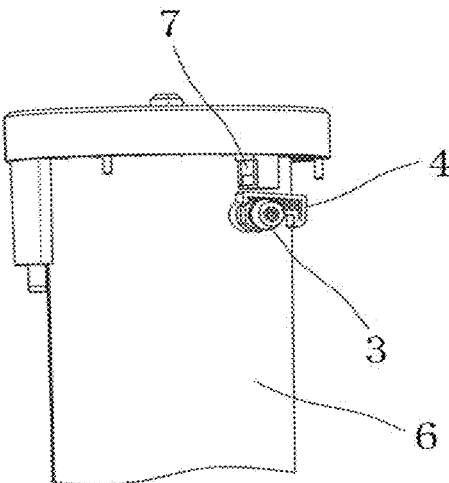
FIG. 4 illustrates a partial perspective view of the fragrance diffuser provided by the embodiment of the disclosure.
Figure 5:
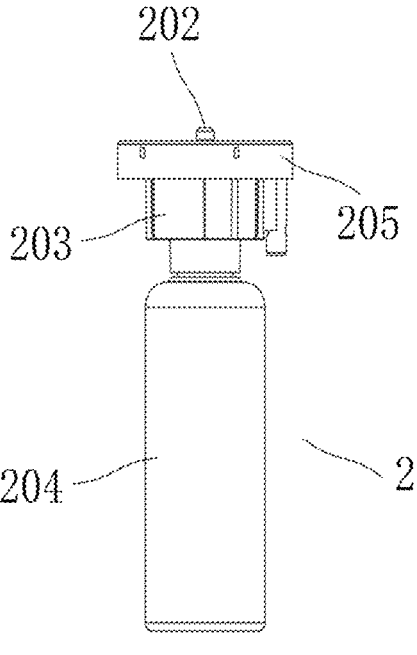
FIG. 5 illustrates a perspective view of an atomizing head assembly provided by the embodiment of the disclosure.
Figure 6:
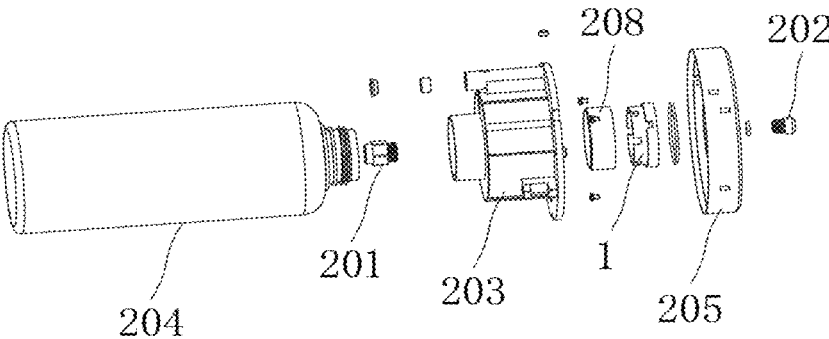
FIG. 6 illustrates an exploded view of the atomizing head assembly shown in FIG. 5.

In another specific embodiment, as shown in FIG. 4, the fragrance diffuser further includes a locking member 3 and an outer shell 5. An inner shell 6 is disposed in the outer shell 5. An engagement groove 7 is defined on an outer side of the inner shell 6 and is protruding outward. An end of the locking member 3 is rotatably penetrated a side wall of the inner shell 6, and the end of the locking member 3 is provided with a locking hook 4. The atomizing head assembly 2 is inserted into the inner shell 6. When the locking hook 4 is engaged with the engagement groove 7, the atomizing head assembly 2 remains stable relative to the inner shell 6. Furthermore, the fragrance diffuser further includes an air pump assembly 8. A base 9 is disposed on a bottom of the outer shell 5. The air pimp assembly 8 is disposed in the outer shell 5 and is connected to the base 9. Specifically, an antiskid pad 10 is disposed on a bottom of the base 9.

In this specification, unless otherwise expressly provided and defined, the term "above" or "below" used to describe the relationship between a first feature and a second feature can mean that the first and second features are in direct contact, or that the first and second features are in indirect contact through an intermediate medium. Moreover, the terms "above", "over" and "on top of" can mean that the first feature is directly above or diagonally above the second feature, or simply that the first feature has a higher horizontal level than the second feature. The terms "below", "under" and "beneath" can mean that the first feature is directly below or diagonally below the second feature, or simply that the first feature has a lower horizontal level than the second feature.

In the description of this specification, the terms "specific embodiment", "another embodiment", "other embodiments", or "specific example", etc., refer to the specific features, structures, materials, or characteristics described in conjunction with these embodiments or examples being included in at least one embodiment or example of the disclosure. In this specification, the illustrative expressions of the above terms do not necessarily refer to the same embodiment or example. Moreover, the specific features, structures, materials, or characteristics described can be combined in a suitable manner in any one or more embodiments or examples. Furthermore, without mutual contradiction, those skilled in the art can combine and integrate different embodiments or examples and the features of different embodiments or examples described in this specification.

Although the embodiments of the disclosure have been shown and described above, it is to be understood that these embodiments are illustrative and should not be construed as limiting the disclosure. Those skilled in the art can make changes, modifications, substitutions, and variations to the above embodiments within the scope of the disclosure.

What is claimed is:

1. An atomizing head baffle, configured to be used in a fragrance device and disposed between an atomizing core and a mist outlet of the fragrance device, wherein the atomizing head baffle comprises a first baffle plate and a second baffle plate, the first baffle plate and the second baffle plate are ring-shaped, and a cover plate is disposed on a top of the first baffle plate and is protruding; the first baffle plate defines first through-holes extending from a lower edge to an upper edge and spaced along a circumferential direction of the first baffle plate, and a number of the first through-holes is at least two; and the second baffle plate defines second through-holes extending from a lower edge to an upper edge and spaced along a circumferential direction of the second baffle plate, and a number of the second through-holes is at least two; and wherein the second baffle plate is sleeved around an outer periphery of the first baffle plate with a fixed overlapping distance along a first direction, thereby reducing each cross sectional area of the second through-holes to form air holes, and the air holes and the first through-holes are configured to pass through atomized particles; and the first direction is a direction oriented from the lower edge of the first baffle plate towards the upper edge of the second baffle plate wherein the first through-holes are spaced from the second through-holes in the first direction, and the lower edge of the second baffle plate is located between the first through-holes and the upper edge of the first baffle plate in the first direction; and a fragrance diffuser comprising an atomizing head assembly, wherein the atomizing head assembly comprises the atomizing head baffle.

2. The atomizing head baffle as claimed in claim 1, wherein a widths of the first through-holes is equal to a width of the second through-holes.

3. The atomizing head baffle as claimed in claim 1, wherein the first through-holes are disposed uniformly along the circumferential direction of the first baffle plate, the second through-holes are disposed uniformly along the circumferential direction of the second baffle plate, the number of the first through-holes is six, and the number of the second through-holes is three.

4. The atomizing head baffle as claimed in claim 1, wherein a widths of each of the air holes and each of the first through-holes is in a range of 6 millimeters (mm) to 12 mm, and a height of each of the air holes and each of the first through-holes is in a range of 2 mm to 6 mm.

5. The atomizing head baffle as claimed in claim 1, wherein a widths of the air holes is in a range of 5.5 mm to 6.5 mm, and a heights of the air holes is in a range of 1.5 mm to 2.5 mm; and a widths of the first through-holes is in a range of 5.5 mm to 6.5 mm, and a heights of the first through-holes is in a range of 4.5 mm to 5.5 mm; or
    wherein the widths of the air holes is in a range of 7.5 mm to 8.5 mm, and the heights of the air holes is in a range of 2.5 mm to 3.5 mm; and the widths of the first through-holes is in a range of 7.5 mm to 8.5 mm, and the heights of the first through-holes is in a range of 5.5 mm to 6.5 mm; or wherein the widths of the air holes is in a range of 8.5 mm to 9.5 mm, and the heights of the air holes is in a range of 2.5 mm to 3.5 mm; and the widths of the first through-holes is in a range of 8.5 mm to 9.5 mm, and the heights of the first through-holes is in a range of 5.5 mm to 6.5 mm; or wherein the widths of the air holes is in a range of 9.5 mm to 10.5 mm, and the heights of the air holes is in a range of 2.5 mm to 3.5 mm; and the widths of the first through-holes is in a range of 9.5 mm to 10.5 mm, and the heights of the first through-holes is in a range of 5.5 mm to 6.5 mm; or wherein the widths of the air holes is in a range of 11.5 mm to 12.5 mm, and the heights of the air holes is in a range of 2.5 mm to 3.5 mm; and the widths of the first through-holes is in a range of 11.5 mm to 12.5 mm, and the heights of the first through-holes is in a range of 5.5 mm to 6.5 mm.

6. The fragrance diffuser as claimed in claim 1, wherein the atomizing head assembly further comprises a main body, an essential oil bottle and a cover, the main body is provided with the atomizing core, a cavity and an air passage, the air passage and the cavity are connected to the atomizing core separately, an atomizing head liner located above the atomizing core is disposed in the cavity, the atomizing head baffle is located in the cavity, and the atomizing head baffle is disposed above the atomizing head liner and is in contact with the atomizing head liner; and wherein a lower end of the main body is connected to the essential oil bottle, and an upper end of the main body is connected to the cover; and the cover is configured to fix the atomizing head baffle and the atomizing head liner in the cavity, and the cover is defined with the mist outlet connected to the cavity.

7. The fragrance diffuser as claimed in claim 1, wherein the fragrance diffuser further comprises a locking member and an outer shell, and an inner shell is disposed in the outer shell; an engagement groove is defined on an outer side of the inner shell and is protruding outward, an end of the locking member is rotatably penetrated a side wall of the inner shell, and the end of the locking member is provided with a locking hook; and the atomizing head assembly is inserted into the inner shell, and the atomizing head assembly remains stable relative to the inner shell when the locking hook is engaged with the engagement groove.

8. The fragrance diffuser as claimed in claim 7, wherein the fragrance diffuser further comprises an air pump assembly, a base is disposed on a bottom of the outer shell, and the air pump assembly is disposed in the outer shell and is connected to the base.

9. The fragrance diffuser as claimed in claim 8, wherein an antiskid pad is disposed on a bottom of the base.

10. The atomizing head baffle as claimed in claim 1, wherein the cover plate is connected with the first baffle plate, and the cover plate further is surrounded by the second baffle plate and thus located inside the second baffle plate.

11. The atomizing head baffle as claimed in claim 1, wherein a lower end of each of the second through-holes facing towards the lower edge of the second baffle plate along the first direction is an open end.

12. An atomizing head baffle, configured to be used in a fragrance device and disposed between an atomizing core and a mist outlet of the fragrance device, wherein the atomizing head baffle comprises a first baffle plate and a second baffle plate, the first baffle plate and the second baffle plate are ring-shaped, and a cover plate is connected onto a top of the first baffle plate; the first baffle plate defines first through-holes extending from a lower edge to an upper edge and spaced along a circumferential direction of the first baffle plate, and a number of the first through-holes is at least two; and the second baffle plate defines second through-holes extending from a lower edge to an upper edge and spaced along a circumferential direction of the second baffle plate, and a number of the second through-holes is at least two;

wherein the second baffle plate is sleeved around an outer periphery of the first baffle plate with a fixed overlapping distance along a first direction, thereby reducing each cross sectional area of the second through-holes to form air holes, the air holes and the first through-holes are configured to pass through atomized particles, and the first direction is a direction oriented from the lower edge of the first baffle plate towards the upper edge of the second baffle plate; and the cover plate is convexly protruded from the top of the first baffle plate along the first direction, and the cover plate further is surrounded by and spaced from the second baffle plate;

wherein the upper edge of the first baffle plate is located between the lower edge of the second baffle plate and the upper edge of the second baffle plate in the first direction, the lower edge of the second baffle plate is located between the first through-holes and the upper edge of the first baffle plate in the first direction, and each cross sectional area of the air holes is determined by a region cooperatively enclosed by a corresponding one of the second through-holes and the upper edge of the first baffle plate; and a fragrance diffuser comprising an atomizing head assembly, wherein the atomizing head assembly comprises the atomizing head baffle.

13. The atomizing head baffle as claimed in claim 12, wherein the first through-holes are spaced from the second through-holes in the first direction.

* * * * *